United States Patent
Purdy

(10) Patent No.: US 7,849,366 B1
(45) Date of Patent: Dec. 7, 2010

(54) METHOD AND APPARATUS FOR PREDICTING YIELD PARAMETERS BASED ON FAULT CLASSIFICATION

(75) Inventor: Matthew A. Purdy, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 733 days.

(21) Appl. No.: 10/810,037

(22) Filed: Mar. 26, 2004

(51) Int. Cl.
*G06F 11/00* (2006.01)

(52) U.S. Cl. .......................................... 714/47; 700/121

(58) Field of Classification Search .................... 714/47, 714/32, 26; 700/110, 121, 109; 438/5
See application file for complete search history.

(56) References Cited

U.S. PATENT DOCUMENTS

| | | | |
|---|---|---|---|
| 3,751,647 A * | 8/1973 | Maeder et al. | 713/401 |
| 5,777,901 A * | 7/1998 | Berezin et al. | 716/19 |
| 6,169,960 B1 * | 1/2001 | Ehrichs | 702/36 |
| 6,265,232 B1 * | 7/2001 | Simmons | 438/14 |
| 6,311,139 B1 * | 10/2001 | Kuroda et al. | 702/81 |
| 6,389,323 B1 * | 5/2002 | Yang et al. | 700/110 |
| 6,496,958 B1 * | 12/2002 | Ott et al. | 716/4 |
| 6,542,830 B1 * | 4/2003 | Mizuno et al. | 702/35 |
| 6,610,550 B1 * | 8/2003 | Pasadyn et al. | 438/14 |
| 6,751,519 B1 * | 6/2004 | Satya et al. | 700/121 |
| 6,947,806 B2 * | 9/2005 | Wang | 700/121 |
| 7,117,057 B1 * | 10/2006 | Kuo et al. | 700/108 |
| 2003/0060916 A1 * | 3/2003 | Hsieh | 700/121 |
| 2004/0029029 A1 * | 2/2004 | Atkinson et al. | 430/30 |
| 2007/0118242 A1 * | 5/2007 | Stine et al. | 700/109 |

* cited by examiner

*Primary Examiner*—Marc Duncan
(74) *Attorney, Agent, or Firm*—Williams, Morgan & Amerson, P.C.

(57) ABSTRACT

A method includes receiving fault classification data associated with a fault condition and estimating at least one yield parameter based on the fault classification data. A system includes a fault classification unit and a yield estimation unit. The fault classification unit is adapted to generate fault classification data associated with a fault condition, and the yield estimation unit is adapted to estimate at least one yield parameter based on the fault classification data.

24 Claims, 4 Drawing Sheets

500 — Receive fault classification data associated with a fault condition

510 — Estimate at least one yield parameter based on the fault classification data

METHOD AND APPARATUS FOR PREDICTING YIELD PARAMETERS BASED ON FAULT CLASSIFICATION

BACKGROUND OF THE INVENTION

1. Field of the Invention

This invention relates generally to the field of semiconductor device manufacturing and, more particularly, to a method and apparatus for predicting yield parameters based on fault classification.

2. Description of the Related Art

There is a constant drive within the semiconductor industry to increase the quality, reliability and throughput of integrated circuit devices, e.g., microprocessors, memory devices, and the like. This drive is fueled by consumer demands for higher quality computers and electronic devices that operate more reliably. These demands have resulted in a continual improvement in the manufacture of semiconductor devices, e.g., transistors, as well as in the manufacture of integrated circuit devices incorporating such transistors. Additionally, reducing the defects in the manufacture of the components of a typical transistor also lowers the overall cost per transistor as well as the cost of integrated circuit devices incorporating such transistors.

The technologies underlying semiconductor processing tools have attracted increased attention over the last several years, resulting in substantial refinements. However, despite the advances made in this area, many of the processing tools that are currently commercially available suffer certain deficiencies. In particular, such tools often lack advanced process data monitoring capabilities, such as the ability to provide historical parametric data in a user-friendly format, as well as event logging, real-time graphical display of both current processing parameters and the processing parameters of the entire run, and remote, i.e., local site and worldwide, monitoring. These deficiencies can engender nonoptimal control of critical processing parameters, such as throughput, accuracy, stability and repeatability, processing temperatures, mechanical tool parameters, and the like. This variability manifests itself as within-run disparities, run-to-run disparities and tool-to-tool disparities that can propagate into deviations in product quality and performance.

Semiconductor devices are manufactured from wafers of a semiconducting material. Layers of materials are added, removed, and/or treated during fabrication to create the electrical circuits that make up the device. The fabrication essentially comprises four basic operations. Although there are only four basic operations, they can be combined in hundreds of different ways, depending upon the particular fabrication process.

The four operations typically used in the manufacture of semiconductor devices are:

layering, or adding thin layers of various materials to a wafer from which a semiconductor device is produced;
patterning, or removing selected portions of added layers;
doping, or placing specific amounts of dopants in the wafer surface through openings in the added layers; and
heat treatment, or heating and cooling the materials to produce desired effects in the processed wafer.

Occasionally, during the fabrication process, one or more process steps are not performed as expected on a production wafer. Such conditions may be due to an error in the fabrication facility automated work flow system (e.g., a database or control script error), a tool failure, or an operator error. If the abnormal process steps occur early during the fabrication process, it is not uncommon for the faulty wafer to undergo many subsequent steps prior to the faulty fabrication being identified. Once a fault is identified further processing is often necessary to determine the nature or cause of the fault, unless the fault is grossly obvious. This process is typically referred to as fault classification. Fault classification may be time consuming and may require significant human intervention.

Processing faults have the potential for degrading the performance of the completed devices. In some cases, the device may function at a lower speed, while in other cases, the device may not be functional at all. Referring to FIG. 1, a simplified diagram of a semiconductor wafer 2 is shown. The semiconductor wafer 2 typically includes a plurality of individual semiconductor die 3 arranged in a grid 4. Typically, electrical or functional tests of the semiconductor die are performed to determine their performance capabilities. Usually, these test are not performed until relatively late in the fabrication process. Functional and non-functional devices are identified to determine the overall yield of the wafer 2 based on the results of the final electrical tests. Yield loss can be defined in terms of whether or not all of the submodules that makeup the device on the die 3 are functional. If one of the submodules is not functional, the entire device may die deemed defective. Yield loss can also be driven by degradations in the performance capabilities of the completed devices. For example, a yield loss may be related to the speed of a device due to the consequences of leakage of the device at those process parameters defined based on a deviation between the measured speed and a target speed.

In the fabrication process, hundreds of processes are performed and at every step it is possible that a fault condition may occur. Some of these faults may affect the yield of the device while others may have little or no impact. Until the actual yield is determined through testing performed at the end of the line, it is difficult to determine the impact of the processing faults. In some cases, a wafer that experienced a serious fault may be processed until completion, yet because of the fault's impact on yield, the value of the devices may be less than the cost of completing the processing.

The present invention is directed to overcoming, or at least reducing the effects of, one or more of the problems set forth above.

SUMMARY OF THE INVENTION

One aspect of the present invention is seen in a method for estimating yield parameters. The method includes receiving fault classification data associated with a fault condition and estimating at least one yield parameter based on the fault classification data.

Another aspect of the present invention is seen in a system including a fault classification unit and a yield estimation unit. The fault classification unit is adapted to generate fault classification data associated with a fault condition, and the yield estimation unit is adapted to estimate at least one yield parameter based on the fault classification data.

BRIEF DESCRIPTION OF THE DRAWINGS

The invention may be understood by reference to the following description taken in conjunction with the accompanying drawings, in which like reference numerals identify like elements, and in which.

Figure 1:
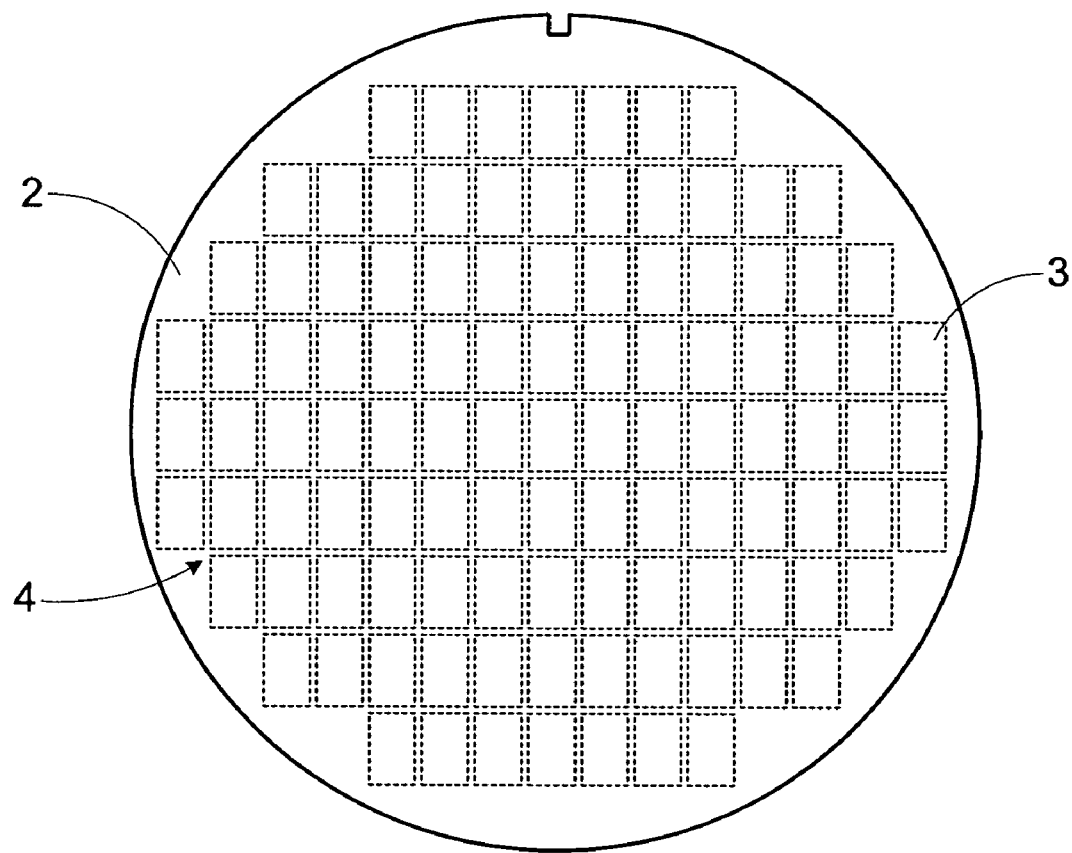
FIG. 1 is a simplified diagram of an illustrative semiconductor wafer.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
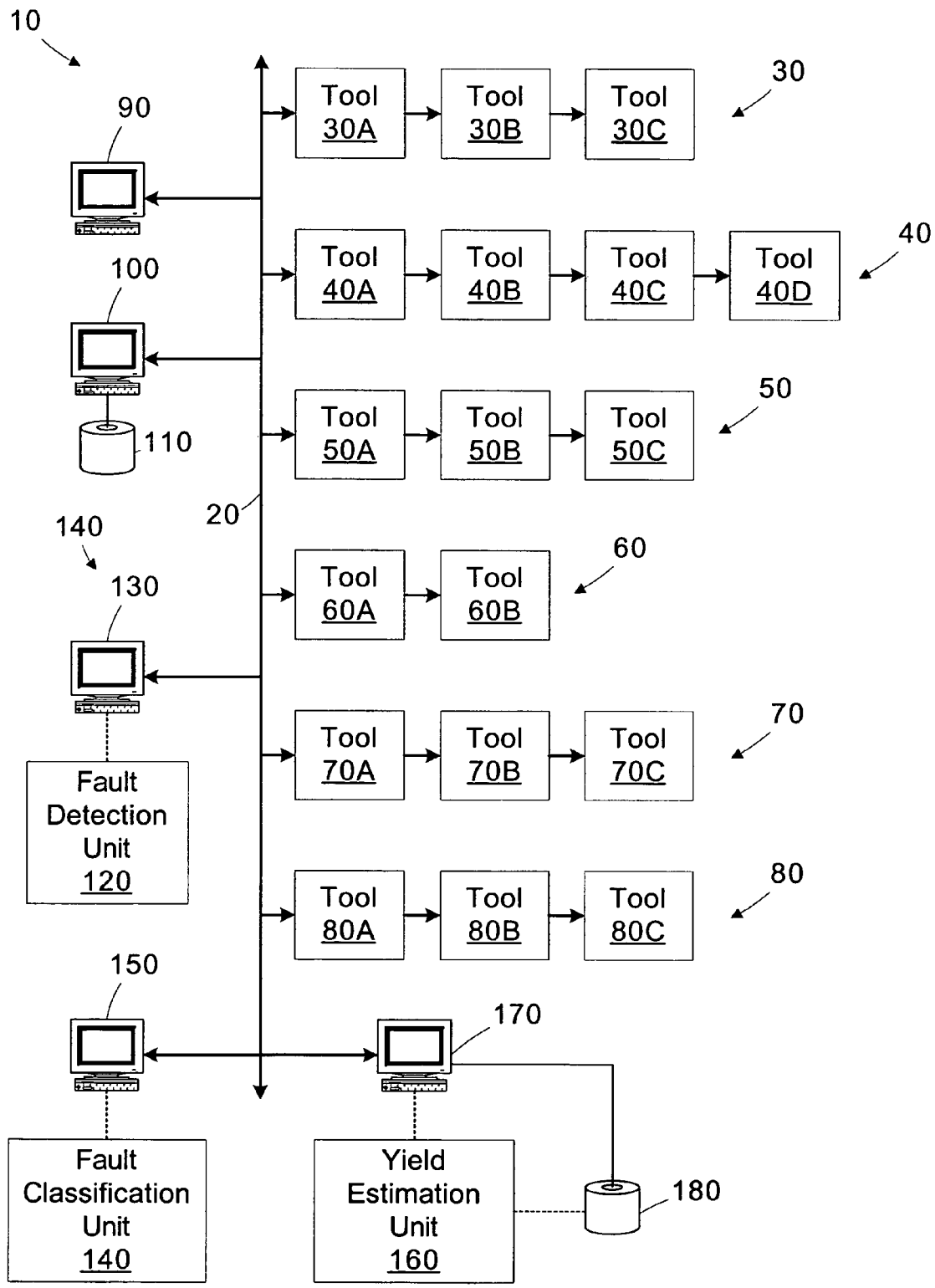
FIG. 2 is a simplified block diagram of a manufacturing system in accordance with one illustrative embodiment of the present invention.

Referring to FIG. 2, a simplified block diagram of an illustrative manufacturing system 10 is provided. In the illustrated embodiment, the manufacturing system 10 is adapted to fabricate semiconductor devices. Although the invention is described as it may be implemented in a semiconductor fabrication facility, the invention is not so limited and may be applied to other manufacturing environments. The techniques described herein may be applied to a variety of workpieces or manufactured items, including, but not limited to, microprocessors, memory devices, digital signal processors, application specific integrated circuits (ASICs), or other devices. The techniques may also be applied to workpieces or manufactured items other than semiconductor devices.

A network 20 interconnects various components of the manufacturing system 10, allowing them to exchange information. The illustrative manufacturing system 10 includes a plurality of tools 30-80. Each of the tools 30-80 may be coupled to a computer (not shown) for interfacing with the network 20. The tools 30-80 are grouped into sets of like tools, as denoted by lettered suffixes. For example, the set of tools 30A-30C represent tools of a certain type, such as a chemical mechanical planarization tool. A particular wafer or lot of wafers progresses through the tools 30-80 as it is being manufactured, with each tool 30-80 performing a specific function in the process flow. Exemplary processing tools for a semiconductor device fabrication environment include metrology tools, photolithography steppers, etch tools, deposition tools, polishing tools, rapid thermal processing tools, implantation tools, etc. The tools 30-80 are illustrated in a rank and file grouping for illustrative purposes only. In an actual implementation, the tools 30-80 may be arranged in any physical order or grouping. Additionally, the connections between the tools in a particular grouping are meant to represent connections to the network 20, rather than interconnections between the tools 30-80.

A manufacturing execution system (MES) server 90 directs the high level operation of the manufacturing system 10. The MES server 90 monitors the status of the various entities in the manufacturing system 10 (i.e., lots, tools 30-80) and controls the flow of articles of manufacture (e.g., lots of semiconductor wafers) through the process flow. A database server 100 is provided for storing data related to the status of the various entities and articles of manufacture in the process flow. The database server 100 may store information in one or more data stores 110. The data may include pre-process and post-process metrology data, tool states, lot priorities, etc.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

The process control server 90 stores information related to the particular tools 30-80 (i.e., or sensors (not shown) associated with the tools 30-80) used to process each lot of wafers in the data store 110. As metrology data is collected related to the lot, the metrology data and a tool identifier indicating the identity of the metrology tool recording the measurements is also stored in the data store 110. The metrology data may include feature measurements, process layer thicknesses, electrical performance, surface profiles, etc. Data stored for the tools 30-80 may include chamber pressure, chamber temperature, anneal time, implant dose, implant energy, plasma energy, processing time, etc. Data associated with the operating recipe settings used by the tool 30-80 during the fabrication process may also be stored in the data store 110. For example, it may not be possible to measure direct values for some process parameters. These settings may be determined from the operating recipe in lieu of actual process data from the tool 30-80.

The manufacturing system 10 includes a fault detection unit 120 executing on a workstation 130 and a fault classification unit 140 executing on a workstation 150. In general, the fault detection unit 120 identifies fault conditions in the manufacturing system 10 and the fault classification unit 140 classifies the identified faults. A yield estimation unit 160 executing on a workstation 170 receives fault classification data from the fault classification unit 140 and generates a yield parameter based on the fault classification.

The distribution of the processing and data storage functions amongst the different computers 90, 100, 130, 150, 170 is generally conducted to provide independence and a central information store. Of course, different numbers of computers and different arrangements may be used. Moreover, the functions of some units may be combined. For example, the fault detection and classification units 120, 140 and/or the yield estimation unit 160 may be combined into a single unit.

In general, the fault detection unit 120 is a model-based, multivariate fault detection analysis engine. The construct and operation of such fault detection tools are known to those of ordinary skill in the art. An exemplary commercially available fault detection engine is ModelWare™ offered by Triant, Inc. of Nanaimo, British Columbia, Canada Vancouver, Canada. The fault detection unit 120 typically predicts values for various characteristics of the processing tool and/or processed wafer, compares the expected data with actual data collected by the tools 30-80 (i.e., or sensors associated with the tools 30-80) and by metrology tools that measure electrical or physical characteristics of the processed wafers, and identifies defects based on the differences therebetween. For clarity and to prevent obscuring the present invention, the fault detection unit 120 is not discussed in greater detail herein.

Similarly, the fault classification unit 140 may have a variety of forms as are known in the art or commercially available. For example, an automated fault classification method that uses an algorithm to define fault classes or a generic automated state recognition system using human defined rules to define fault classes may be used. An exemplary automatic fault classification technique is described in U.S. patent application Ser. No. 10/682,019, entitled "Method and Apparatus for Fault Classification Based on Residual Vectors," by Matthew A. Purdy, Robert J. Chong, Gregory A. Cherry, and Richard J. Markle, and incorporated herein by reference in its entirety.

The fault classification unit 140, in accordance with the above cited patent application, uses fault detection data to separate faults into different categories, or "bins." Typically, each of the fault classes corresponds to a specific fault mechanism on the associated tool, such as a failure of an electrostatic chuck for holding a wafer, a failure in the gas system, a failure in the RF power system, etc. Each of these fault mechanisms may have a characteristic impact on yield parameters, such as overall yield, defectivity, or device performance.

The yield estimation unit 160 receives the fault classification data from the fault classification unit 140 and employs a yield estimation database 180 to match fault classes to estimated yield parameters. Although the yield estimation database 180 is illustrated as a separate entity, it may exist as part of the central data store 110. The yield estimation unit 160 may use one or more yield-related effects models to predict one or more yield parameters, such as overall yield, speed, defectivity, etc.

Figure 3:
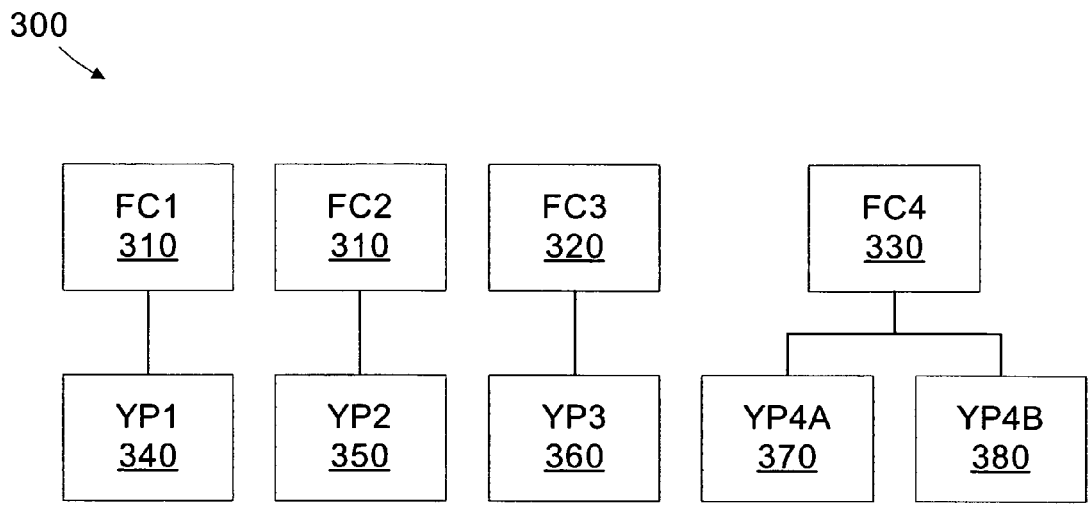
FIGS. 3 and 4 are diagrams illustrating various embodiments for organization of a yield estimation database used in the system of FIG. 2.

The yield estimation unit 160 may quantify yield impact in a variety of ways. In one embodiment, the yield estimation unit 160 may estimate the impact of a fault in a given fault class on systematic yield (e.g., yield related to how the device functions), defect based yield (e.g., whether the device functions at all), or both. The yield estimation unit 160 may quantify the yield impact as the number of die lost, the percentage of yield loss compared to material that did not have the fault, a speed likelihood or distribution, etc. As shown in FIG. 3, in one hierarchy 300 for the yield estimation database 180, for each fault class (FC) 310-330 there is are associated yield parameters (YP) 340-380. Certain fault classes, e.g., FC4 330 may have more than one associated yield parameter, e.g., YP4A 370 and YP4B 380 to address the situation where a particular fault affects yield in a more than one way (e.g., overall yield impact and speed impact).

The yield estimation unit 160 may use correlations between fault class and yield impact that are developed and updated in an automated fashion based on historical data. For example, any time a lot is sorted (i.e., its yield is determined), the estimates for yield impact of any fault classes that wafer encountered could be updated. For example, a yield loss estimate for a given fault class (e.g., FC1 310) may be 10%. If a current wafer having a fault in the same class has a yield loss of 15%, the yield parameter estimate (e.g., YP1 340), tracked by the yield estimation unit 160 for the fault class may be updated using an averaging technique (e.g., straight average, weighted average, exponentially weighted average, etc.).

Figure 4:
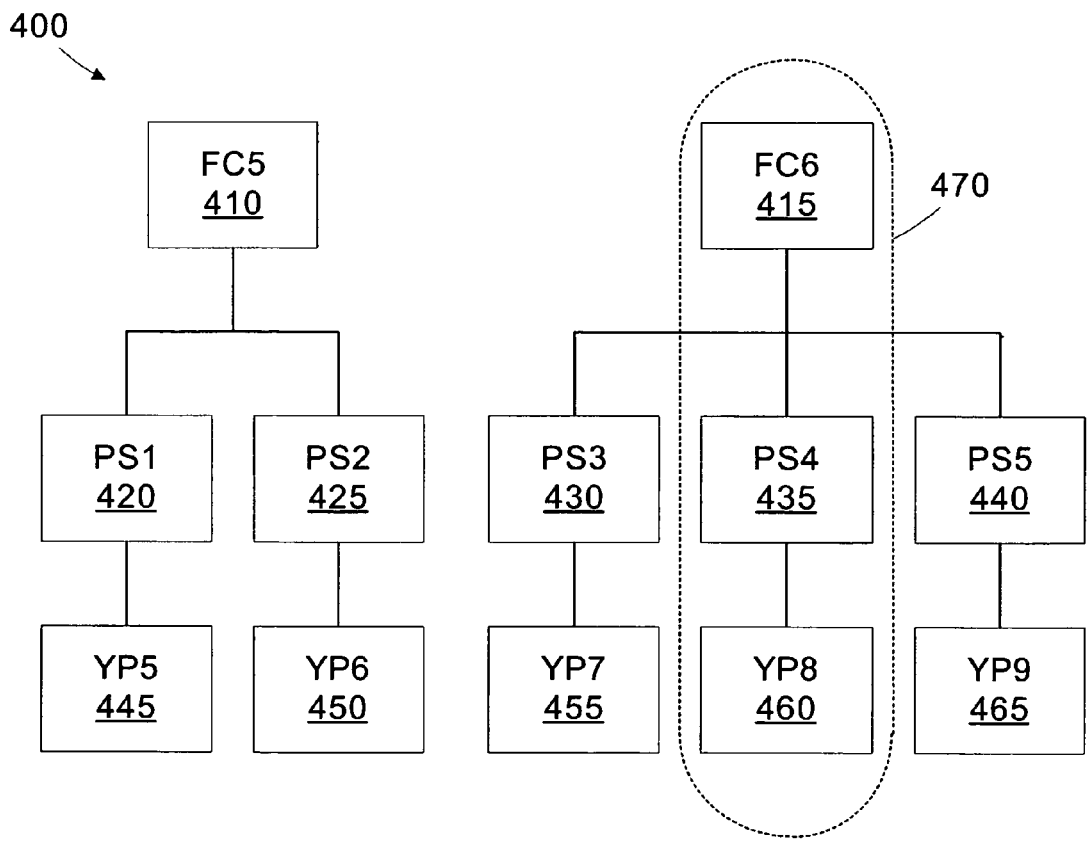

In some cases, as illustrated in the hierarchy 400 of FIG. 4, context data regarding the particular process being performed may be included in the analysis by the yield estimation unit 160. For example, a particular tool type may be used to perform multiple different processes on a wafer during the fabrication process. A fault at one step may have a different impact on yield than a similar fault occurring at a different step. For each fault class (FC) 410, 415 and process/step (PS) 420-440 combination, one or more yield parameters (YP) 445-465 may be tracked in the yield estimation database 180. Hence, the yield estimation unit 160 may generate separate yield threads for each process/step and potential fault condition. For example, a yield thread 470 would include FC6 420, PS4 435, and YP8 460.

The yield estimation unit 160 may track yield estimates for a given wafer or lot individually by fault occurrence. For example, the yield estimation unit 160 may generate a report for the wafer listing all the faults experienced and yield estimates for each fault class. In another embodiment, the yield estimation unit 160 may combine the yield estimates for the individual faults to generate an overall yield estimate. Various techniques may be employed for combining the yield estimates. For example, if the yield impacts are determined as a number of die lost for each fault classification, the yield estimation unit 160 may combine the impact by calculating a sum of all anticipated die lost. If the yield impacts are determined as an expected percent yield loss, then the yield estimation unit 160 may combine the impact by calculating the product of expected yield from each fault classification. Expected yield is calculated as 1 minus the percent yield loss.

Based on the yield estimates, the yield estimation unit 160 may implement automatic actions, or may recommend possible actions to an operator or fabrication manager. The particular actions taken upon identifying a fault class with an associated yield correlation may depend on the particular correlation. If the fault class signifies an increase in yield loss related to defectivity outside a predetermined acceptable range, the yield estimation unit 160 may recommend removing the processing tool 30-80 from production for maintenance. If the fault class has an associated significant overall yield loss, the yield estimation unit 160 may recommend canceling any future processing on the wafer (i.e., scraping the wafer), because the predicted future economic value of the devices on the wafer is less than the expected cost to process the wafer to the end of the line.

Figure 5:
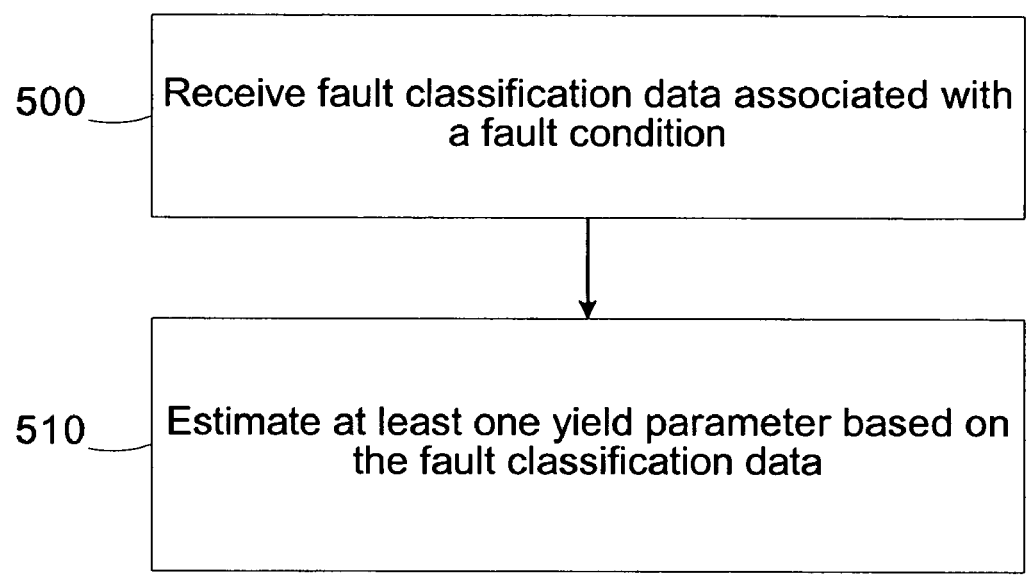
FIG. 5 is a simplified flow diagram of a method for predicting yield parameters based on fault classification in accordance with another illustrative embodiment of the present invention.

Turning now to FIG. 5, a simplified flow diagram of a method for predicting yield parameters based on fault classification in accordance with another illustrative embodiment of the present invention is provided. In block 500, fault classification data associated with a fault condition is received. In block 510, at least one yield parameter is estimated based on the fault classification data.

By estimating the impact of faults on yield parameters during the fabrication process, the yield estimation unit 160 allows operators or fabrication supervisors to take appropriate actions prior to the end-of-line yield testing. Problematic tools may be scheduled for maintenance to reduce the yield impacts on subsequent wafers and wafers that have been significantly degraded may be scrapped, thereby reducing subsequent resource expenditures.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method, comprising:
   receiving fault classification data associated with a tool fault condition, the tool fault condition being associated with a process tool for processing a wafer; and
   estimating at least one yield parameter of the wafer based on the fault classification data, wherein estimating the at least one yield parameter further comprises estimating a performance yield parameter, and the performance yield parameter further comprises a speed yield parameter.

2. The method of claim 1, wherein estimating the at least one yield parameter further comprises estimating an overall yield parameter.

3. The method of claim 2, wherein estimating the overall yield parameter further comprises estimating a number of die lost.

4. The method of claim 2, wherein estimating the overall yield parameter further comprises estimating a percentage of die lost.

5. The method of claim 1, wherein estimating the at least one yield parameter further comprises associating at least one estimated yield parameter with a fault class specified by the fault classification data.

6. The method of claim 5, further comprising:
   determining an actual yield parameter for a wafer; and
   updating the estimated yield parameter based on the actual yield parameter.

7. The method of claim 1, further comprising removing the process tool associated with the tool fault condition from service responsive to the estimated yield parameter being outside a predetermined range.

8. The method of claim 1, further comprising scrapping the wafer responsive to the estimated yield parameter being outside a predetermined range.

9. The method of claim 1, further comprising:
   determining process/step data associated with the tool fault condition; and
   estimating at least one yield parameter based on the fault classification data and the process/step data.

10. The method of claim 9, further comprising estimating a plurality of yield parameters based on the fault classification data and the process/step data.

11. The method of claim 1, further comprising estimating a plurality of yield parameters based on the fault classification data.

12. A system, comprising:
    a fault classification unit adapted to generate fault classification data associated with a tool fault condition, the tool fault condition being associated with a process tool for processing a wafer; and
    a yield estimation unit adapted to estimate at least one yield parameter of the wafer based on the fault classification data, wherein the at least one yield parameter further comprises a performance yield parameter, and the performance yield parameter further comprises a speed yield parameter.

13. The system of claim 12, wherein the at least one yield parameter further comprises an overall yield parameter.

14. The system of claim 13, wherein the overall yield parameter further comprises an estimated number of die lost.

15. The system of claim 13, wherein the overall yield parameter further comprises an estimated percentage of die lost.

16. The system of claim 12, further comprising a yield estimation database adapted to store data associating at least one estimated yield parameter with a fault class specified by the fault classification data, wherein the fault estimation unit is further adapted to access the fault classification database to estimate the at least one yield parameter.

17. The system of claim 16, wherein the yield estimation unit is further adapted to receive an actual yield parameter for a wafer and update the estimated yield parameter based on the actual yield parameter.

18. The system of claim 12, wherein the yield estimation unit is further adapted to recommend removing the process tool associated with the tool fault condition from service responsive to the estimated yield parameter being outside a predetermined range.

19. The system of claim 12, wherein the yield estimation unit is further adapted to recommend scrapping the wafer responsive to the estimated yield parameter being outside a predetermined range.

20. The system of claim 12, wherein the yield estimation unit is further adapted to determine process/step data associated with the tool fault condition and estimate at least one yield parameter based on the fault classification data and the process/step data.

21. The system of claim 20, wherein the yield estimation unit is further adapted to estimate a plurality of yield parameters based on the fault classification data and the process/step data.

22. The system of claim 12, wherein the yield estimation unit is further adapted to estimate a plurality of yield parameters based on the fault classification data.

23. A method, comprising:
    receiving fault classification data associated with a fault condition; and
    estimating at least one speed yield parameter based on the fault classification data.

24. A system, comprising:
    a fault classification unit adapted to generate fault classification data associated with a fault condition; and
    a yield estimation unit adapted to estimate at least one speed yield parameter based on the fault classification data.

* * * * *